United States Patent [19]

Vance et al.

[11] Patent Number: 5,541,158
[45] Date of Patent: Jul. 30, 1996

[54] METHOD FOR INCREASING THE HEMATOCRIT OF A NORMAL MAMMAL

[75] Inventors: John F. A. Vance, Stowe, Vt.; Robert I. Abels, Westfield, N.J.; Freedolph D. Anderson, Neshanic Station, N.J.; William L. Harris, Port Murray, N.J.; Dorothy Thompson, Hulmeville, Pa.

[73] Assignee: Ortho Pharmaceutical Corporation, Raritan, N.J.

[21] Appl. No.: 409,223

[22] Filed: Sep. 19, 1989

Related U.S. Application Data

[63] Continuation-in-part of Ser. No. 36,646, Apr. 10, 1987, abandoned.

[51] Int. Cl.$^6$ .......................... A61K 38/16; A61K 35/14; A01N 37/18; C07K 1/00
[52] U.S. Cl. .................... 514/8; 514/2; 514/21; 530/380; 530/397
[58] Field of Search ............... 514/8, 2, 21; 530/397, 530/380

[56] References Cited

U.S. PATENT DOCUMENTS 5,013,718  5/1991  Adamson et al. ........................ 514/8

FOREIGN PATENT DOCUMENTS 2171303  8/1986  United Kingdom.
2171304  8/1986  United Kingdom.

OTHER PUBLICATIONS

Hauer et al. (1984) Vox Sang. 46:8–12.
Udupa et al. (1984) J. Lab. Clin. Med. 103:574–580.
Egrie et al. (1985) Prog. Clin. Biol. Res. 191:339–350.
Rodgers et al. (1975) Proc. Soc. Exp. Biol. Med. 148:380–382.
Schustack et al. (1985) Clin. Nephrology 23(6):303–306.
Hedstrand et al. (1977) Scand. J. Haematol. 19:417–423.
Cottino et al. (1985) Acta Gerontol. 35(3/4):217–222 (abstract only).
Maeda et al. (1989, Jul. 29) The Lancet 2(8657):284.
Levine et al. (1988) Surgery 104:365–369.
Masunaga et al., Acta Haematol JPN, 49(4):807–815 (1986).
Essers et al., Proc. Eur. Dial. Transplant Assoc., 11:398–402 (1974).
Winearls et al., Lancet, pp. 1175–1178 (Nov. 22, 1986).
Eschbach et al., N. Eng. J. Med., 316:73–78 (1987).
Eschbach et al, J. Clin. Invest., 74:434–441 (1984).
Egrie et al., Immunobiol., 172:213–224 (1986).
Spivak et al., Johns Hopkins Med. J., 146:311–320 (1980).
Schustack et al., Clin. Nephrol., 23(6):303–306 (1985).
Estrella et al., Clinica Chimica Acta, 164:1–6 (1987).
Hedstrand et al., Scand. J. Haematol., 19(5):417–423 (1977).
Udupa et al., J. Lab. Clin. Med., 103(4):574–580 (1984).
Feleppa, Scand. J. Haemat., 10:186–188 (1973).
Feleppa, Pharm. Res. Comm., 4(4):363–367 (1972).
Beru et al., J. Biol. Chem., 260(16):9251–9257 (1985).
Rotruck et al., J. Agric. Food Chem., 27(1):27–33 (1979).
Kickler et al., JAMA, 260(1):65–67 (1988).
Levine et al., J. Trauma, 29(8):1134–1139 (1989).
Maeda et al., Lancet, p. 284 (Jul. 29, 1989).
Schwenk et al., DICP, 23(7–8):528–536 (1989).
Levine et al., Surgery, 104(2):365–369 (1988).
Goodman & Gilman's, The Pharmacological Basis of Therapeutics, 7th Ed., pp. 1131–1134 (1985).

*Primary Examiner*—Robert A. Wax
*Assistant Examiner*—Lisa J. Hobbs
*Attorney, Agent, or Firm*—John W. Wallen, III

[57] ABSTRACT

A method for increasing the hematocrit of a normal mammal using erythropoietin (EPO) is provided. The method comprises the steps of administering to the mammal a hematocrit increasing effective amount of EPO, in a pharmaceutically acceptable form. Additionally administered is an effective amount of iron, in a pharmaceutically acceptable form, sufficient to increase the serum iron content of the mammal to an erythropoiesis supportable level. The method is useful for increasing the amount of blood that can be donated for transfusion purposes, in particular autologous transfusion.

22 Claims, 4 Drawing Sheets

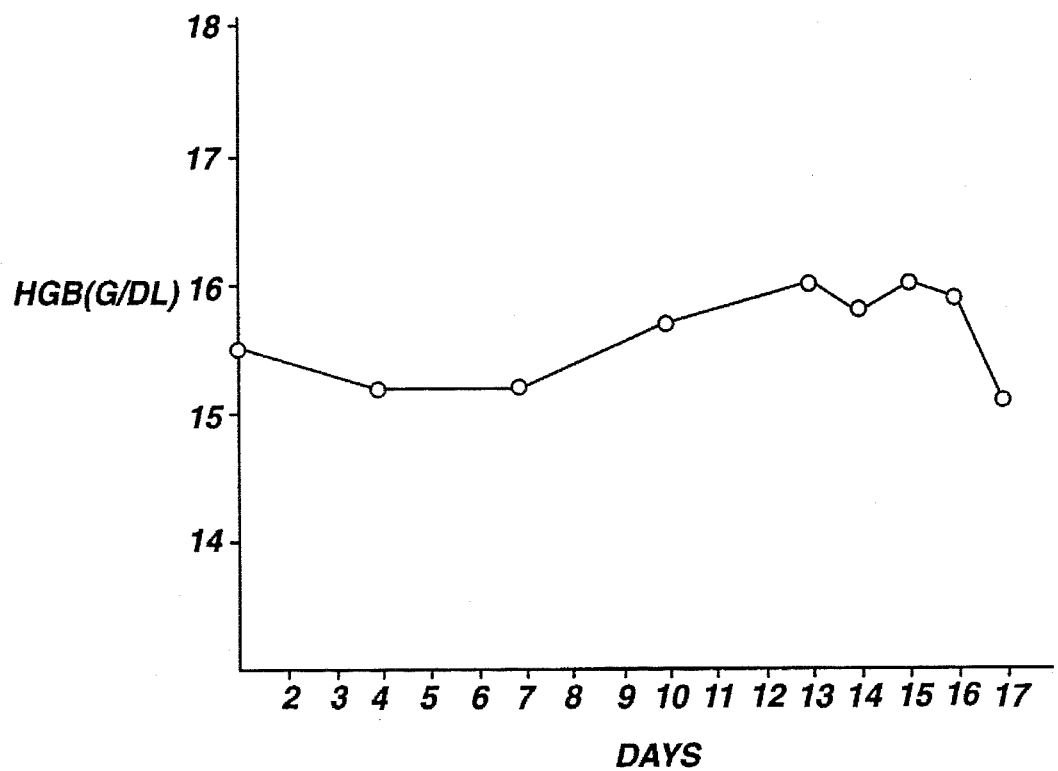
FIG. 1A  HEMATOLOGIC PARAMETERS IN ERYTHROPOIETIN TREATED SUBJECTS PRIOR TO IRON LOADING

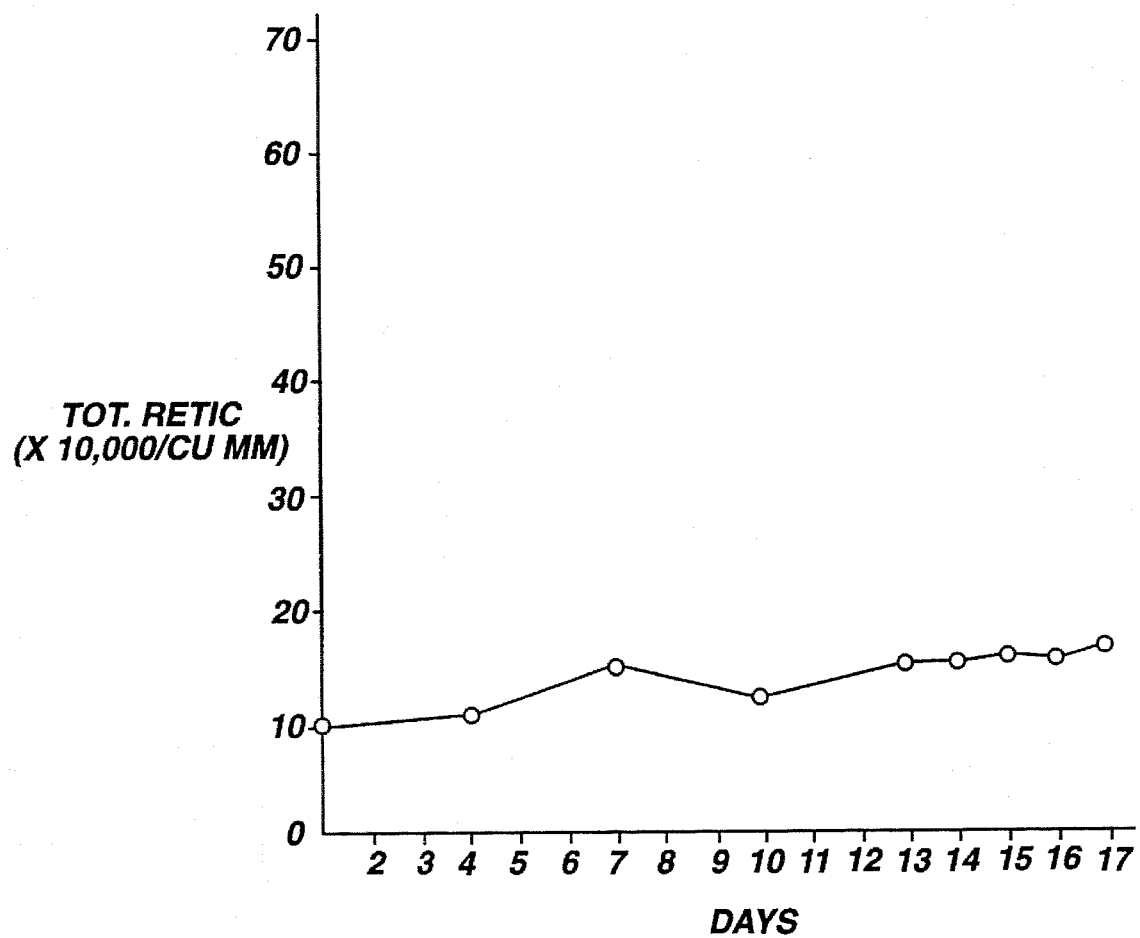
FIG. 1B  HEMATOLOGIC PARAMETERS IN ERYTHROPOIETIN TREATED SUBJECTS PRIOR TO IRON LOADING

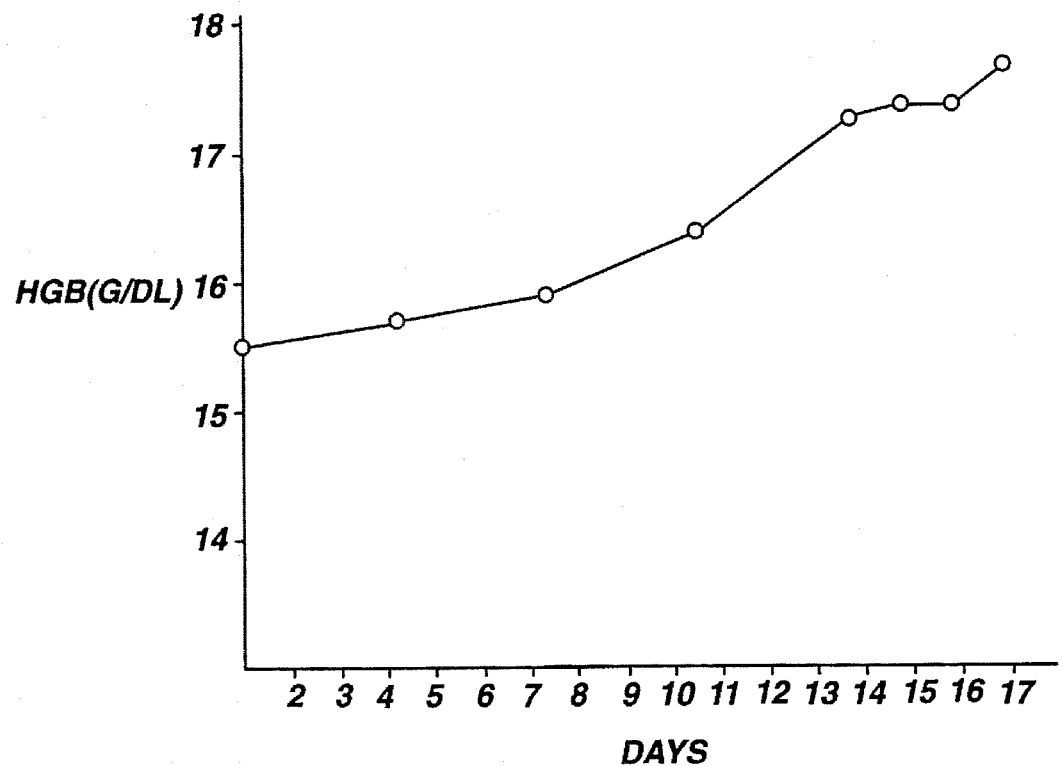
FIG. 2A HEMATOLOGIC PARAMETERS IN ERYTHROPOIETIN TREATED SUBJECTS AFTER IRON LOADING

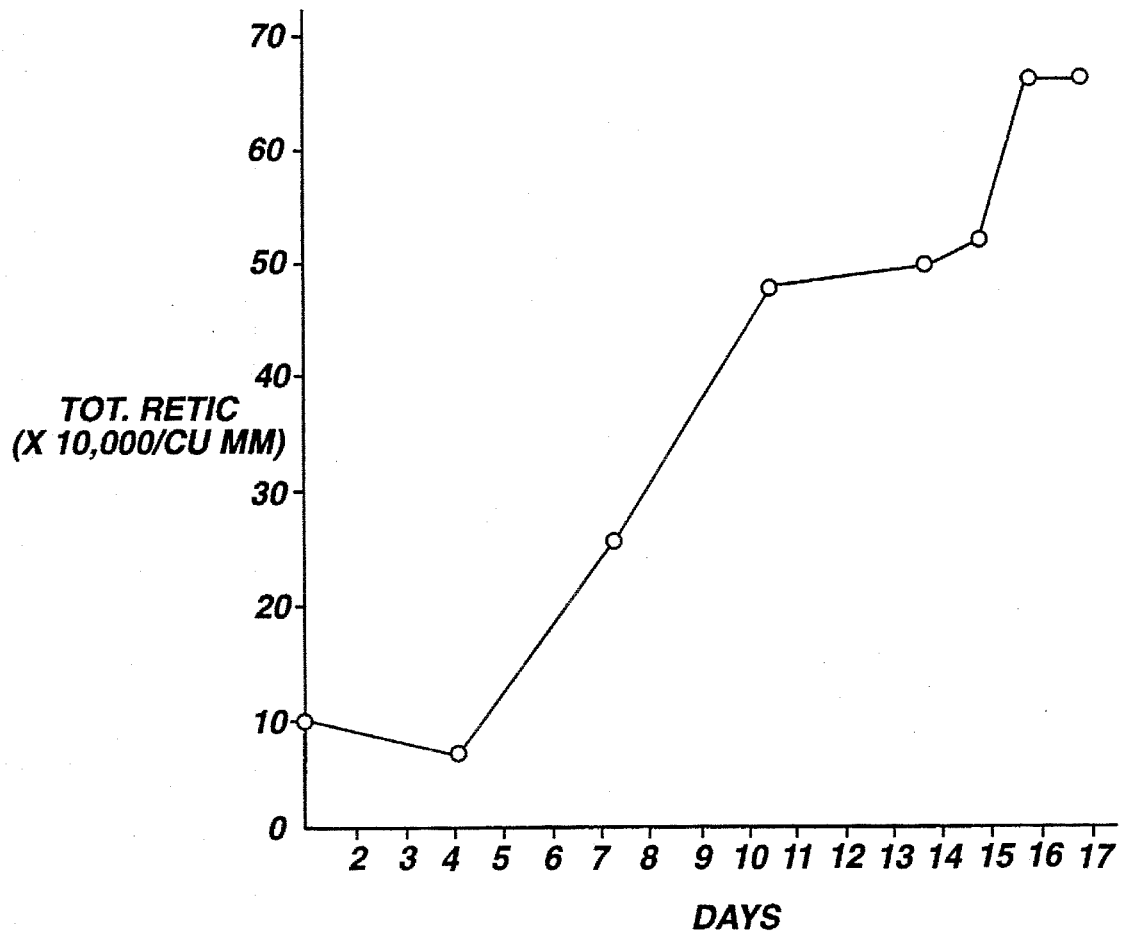
FIG. 2B HEMATOLOGIC PARAMETERS IN ERYTHROPOIETIN TREATED SUBJECTS AFTER IRON LOADING

METHOD FOR INCREASING THE HEMATOCRIT OF A NORMAL MAMMAL

BACKGROUND OF THE INVENTION

This application is a continuation-in-part of U.S. Ser. No. 036,646, filed Apr. 10, 1987, now abandoned, the contents of which are hereby incorporated by reference into this application.

The present invention relates to a method for increasing the hematocrit and the rate of erythropoiesis of a normal mammal and specifically relates to a method for doing so by administering effective amounts of erythropoietin and iron.

It has long been the practice in both pre and post-operative therapy to attempt to expand the patient's red blood cell population. Typically, such red blood cell expansion has been achieved by the transfusion of homologous blood received from various donors. Recently, however, there has been heightened concern about the safety of homologous transfusion, aroused by the discovery that acquired immunodeficiency syndrome (AIDS) as well as other infectious diseases such as hepatitis, can be transferred by blood transfusions. Further, the present method of screening blood donors does not entirely eliminate the possibility of transfusion transmitted infections in donated homologous blood. For instance, tests for non-A, non-B Hepatitis have been found to be relatively unreliable and tests for antibody to the AIDS virus have failed to detect blood donors with viremia.

Accordingly, interest in recent years has increased in red blood cell expanding techniques other than homologous transfusion, and specifically in so-called autologous transfusion.

Autologous transfusion has been accomplished in the past by essentially two ways: 1) through the intraoperative salvage and retransfusion of the patient's blood during surgery; and 2) through donation by the patient of the required amount of blood before surgery i.e. pre-deposit or pre-donation. The clinical and laboratory procedures used in collecting, preserving and transfusing autologous blood are the same as those used routinely in providing homologous blood to patients. Such procedures require administration arrangements for gaining access to the medical services and for insuring that the autologous blood, once collected, gets to the correct patient who pre-deposited it. Prior to the present invention, a major problem with autologous transfusion has been the inability to obtain the required amount of blood due to induction of anemia (hematocrit less than 34%) by phlebotomy.

Accordingly, there is a need for a less inconvenient but satisfactory alternative to homologous blood transfusion. Use of the present invention prevents or attenuates the induction of anemia which occurs when blood is withdrawn for transfusion and hence allows the collection of the required number of units of blood, particularly in patients with a low baseline hematocrit.

SUMMARY OF THE INVENTION

In accordance with the present invention, a method is provided as an alternative to homologous blood transfusion which method avoids the risk of the patient's receiving contaminated homologous transfusions. Use of the present method prevents or attenuates the drop in hematocrit due to phlebotomy and permits the patient to pre-donate greater amounts of blood for transfusion purposes, in particular autologous transfusion.

Specifically, it has now been discovered that the hematocrit and rate of erythropoiesis of normal mammals, such as humans, may be increased by administering to the mammal a hematocrit increasing effective amount of erythropoietin, in a pharmaceutically acceptable form. The erythropoietin is administered in conjunction with the step of administering to the mammal, iron, in a pharmaceutically acceptable form and in an amount sufficient to increase the serum iron content to an erythropoiesis supportable level. Thus, for example, the hematocrit may be maintained at an acceptable level while withdrawing blood for autotransfusion techniques.

Prior to the discovery associated with the present invention, it was suggested that the administration of erythropoietin (EPO) is beneficial in EPO deficient patients. Early studies of the effect of EPO-rich plasma in patients with end-stage renal disease have been reported with variable results (Esser, U. et al. Proc. Eur. Dial. Transp. Ass., 1974, 11:398–402). These prior methods of using EPO have been confined to the treatment of diseased or unhealthy individuals, especially those exhibiting anemia and having low hematocrits. It has heretofore been thought that EPO therapy would not be useful for normal individuals, i.e. those individuals who are non-anemic and have a normal hematocrit (i.e., greater than about 34%). In fact, the potential benefit of EPO therapy to correct anemia was doubted because of the concern that erythropoietin inhibitors might block the effect of the EPO. Such doubt about EPO treatment in normal mammals was apparently confirmed in our early experiments, wherein EPO treated mammals failed to respond. This doubt was unexpectedly extinguished, however, with our discovery that by employing, in conjunction with EPO, iron, in an amount sufficient to support erythropoiesis, a dramatic increase in the hematocrit of EPO treated normal subjects resulted.

BRIEF DESCRIPTION OF THE DRAWINGS

FIGS. 1A and B depict the hematologic parameters of erythropoietin treated subjects prior to employing the teachings of this invention; and FIGS. 2A and B depict the hematologic parameters of erythropoietin treated subjects after treatment in accordance with this invention.

DETAILED DESCRIPTION OF THE INVENTION

The present invention provides a method for increasing the hematocrit, and the rate of erythropoiesis of a normal mammal by treating said mammal with effective amounts of iron and EPO.

The hematocrit is a measure of the red blood cell mass of a mammal's blood and is generally determined by simply loading a sample of whole blood into a capillary tube and centrifuging the tube to pack red blood cells in the bottom of the tube. The volume of packed red blood cells is then compared to the total volume of whole blood. In general, in normal (i.e., non-anemic) and otherwise healthy, grown, human females, hematocrit levels are greater than 37% and for normal human males the hematocrit levels are greater than 42%. For the purposes herein, anemia shall be defined as a hematocrit which is less than about 34%. A more direct measurement of the rate of erythropoiesis is the total reticulocyte count in the blood expressed as the total cells per unit volume. Normal levels for grown humans are approximately $50$–$150 \times 10^3$ cells/mm$^3$. As described herein, the present invention increases the hematocrit and reticulocyte count above the normal levels and hence is useful as an alternative to homologous transfusions or the current autologous transfusion techniques. By employing the present methods, the reticulocyte content of a patient's blood may be increased by as much as ten-fold over normal levels.

Various forms of erythropoietin exist and any of them may be used in the present methods. The erythropoietin employed in the present invention is a 30,400 dalton glycoprotein hormone which is produced in the adult kidney and which is responsible for maintaining the body's red blood cell (erythrocyte) mass at an optimal level. EPO has an activity which stimulates erythropoiesis (i.e. the formation of red blood cells) resulting in the differentiation of blood stem cells into red blood corpuscles. Because of this activity, EPO has been widely examined as a therapeutic in the clinical treatment for those disorders characterized by low or defective red blood cell production, such as anemia, and in particular renal anemia. However, such investigations were limited prior to the advent of recombinantly produced EPO because of the unavailability of large amounts of pure, human EPO.

An example of the earlier method of obtaining EPO by purification of urine is described in U.S. Pat. No. 4,397,840. Methods for producing human EPO by recombinant DNA techniques are described in International Patent Application Publication Nos. WO 85/02610 and WO 86/03520. Recombinant techniques for producing EPO provide the advantage of a source of relatively pure EPO which can be produced in large quantities inexpensively. Recombinant monkey EPO has been produced also and shown to elevate the hematocrit of Balb C mice (see Egrie, J. C. et al., Prog. Clin. Bio. Res., 1985, 191:339–50). The EPO of choice is the recombinantly derived human EPO described in the above publication.

It is contemplated that biologically active fragments, analogs, or chemically synthesized derivatives of EPO may be used in the present methods rather than the naturally occurring molecule produced by recombinant DNA techniques, provided that such fragments or derivatives retain the biological activity of naturally occurring EPO. Certain EPO analogs are described in U.S. Pat. No. 4,703,008. Therefore, use of such biologically active EPO analogs, fragments or derivatives is considered to be within the scope of the present invention, provided that such analogs, fragments or derivatives possess the biological activity of causing bone marrow cells to increase production of reticulocytes and red blood cells, and to increase hemoglobin synthesis or iron uptake. As used herein, "erythropoietin" shall include such fragments, analogs or derivatives.

In practicing the present invention, the EPO is preferably administered to the subject parenterally. Suitable routes of parenteral administration are intravenous, intramuscular and subcutaneous injection. The EPO may be administered in any pharmaceutically acceptable form, such as a physiologically buffered solution. A suitable physiological buffered solution is an isotonic saline solution having a pH of about 7.6. at 1:10 dilution.

Although at the present time, EPO is only available in parenteral dosage forms, it is envisioned that oral dosage forms of EPO may become available in the future. Thus, oral administration of EPO is considered to be within the scope of the present invention. Such oral dosage forms would be designed to provide effective blood levels of EPO similar to the present parenteral dosage forms. Such oral dosage forms may be in the form of a coated tablet, such as enteric coated tablets, to prevent degradation of the EPO by gastric acid and enzymes. Additionally, new forms of EPO may be made to produce a more lipophilic chemical derivative of EPO. A more lipophilic derivative is more rapidly absorbed so that the residency time in the degradative gastric medium is minimized.

The amount of EPO administered to the subject is an amount sufficient to effectively increase the hematocrit level of that subject. Thus, for a normal adult male it is that amount which increases the hematocrit above the level existing in that individual before EPO therapy was begun. For example, use of the present method may increase the subject's hematocrit by about 10% over a period of two weeks. In general, a hematocrit increasing effective amount of EPO is in the range of about 15–1500 units per kilogram of body weight (U/kg) as a single dose given several days each week. Preferably, the dose is in the range 100–700 U/kg as a single dose administered several times weekly.

It has been discovered that the EPO must be administered to the normal subject in conjunction with iron, if the subject's iron stores are low prior to the start of therapy, in order to achieve an increase in the hematocrit. The iron may be administered in any pharmaceutically acceptable form. Oral preparations of ferrous sulfate are preferred, in the form of a tablet, elixir, syrup or oral solution. Any of the various ferrous salts, as hydrated or dry salts, may be used as alternatives to the sulfate salt. Such salts include fumarate, gluconate, succinate, glutamate, lactate, citrate, tartrate, pyrophosphate, cholinisocitrate, and carbonate. Reduced iron (metallic iron, elemental iron) in the form of carbonyl iron powder may also be used. Reducing agents (e.g., ascorbic acid) and some chelating agents (e.g., succinic acid or sulfur containing amino acids) may be added to the iron formulation to increase absorption of the ferrous iron. Parenteral preparations of iron such as solutions of iron dextran, iron sorbitex, green ferric ammonium citrate, ferrous gluconate, iron adenylate and iron polyisomaltose may also be used.

The preferred route of administration for the iron is oral due to various disadvantages inherent in the parenteral preparations. However, circumstances may exist where the parenteral route is preferred. In particular, the iron may be administered parenterally when in mixture with the EPO.

The amount of iron to be administered must be sufficient to increase the available iron to a level sufficient to support erythropoiesis. Iron available for erythropoiesis is in the form of serum iron loosely bound to transferrin, a glycoprotein B-globulin which transports iron throughout the blood stream and, in particular, transports iron to the bone marrow for erythropoiesis. The primary source of transferrin bound iron is dietary iron which is generally absorbed in the small intestine (most easily in the ferrous form) and then passed into and through the mucosal cells of the small intestine directly into the blood stream where it immediately is bound to the transferrin. A secondary source of iron is available in the form of ferritin, a stored form of iron consisting of ferric hydroxide-ferric phosphate and attached to a protein called apoferritin.

In normal humans, the quantity and total capacity of transferrin to bind iron generally greatly exceeds the amount of iron actually bound. For example, transferrin concentrations in normal sera are in the range of 0.2 to 0.4 g/100 ml. Normally, the absolute transferrin concentration is not determined but instead is expressed in terms of the capacity of the transferrin to bind iron, i.e. the quantity of iron that could be bound if all the transferrin were saturated with iron. The term employed for this saturation capacity is the total iron binding capacity (TIBC). Accordingly, the percent saturation of transferrin is the serum iron expressed as a percentage of the TIBC. Normal ranges for such percent saturation in humans are from about 20–55%.

Without being bound by such theory, based on our work it is now believed that once an effective amount of EPO is present in a mammal's blood, the controlling parameter affecting the rate of erythropoiesis is the available iron bound to transferrin which in turn may be expressed as the percent saturation of transferrin. It follows then that for EPO therapy to be effective in the normal individual, the percent saturation level of transferrin may have to be increased above such individual's normal levels. For example, the percent saturation level may be increased by a factor of about 1.2–3.0 in order to achieve a level high enough to support erythropoiesis. Preferably, such levels would be increased by a factor in the range 1.5–2.5.

In most normal humans, iron administered at the rate of 100–1500 mg per day will produce the requisite increase in saturation levels. Preferably, the iron should be administered at the rate of 300–900 mg per day. The iron therapy should begin about 1–21 days prior to EPO therapy. Preferably, iron therapy is begun 14 days before EPO therapy and continued throughout the entire treatment period. It will be understood that the choice of therapy is dependent on such factors as the iron status of the individual as well as any other precondition.

Various treatment regimens may be used in the practice of the present invention. One treatment regimen which may be used is as follows. A suitable amount of iron sufficient to increase or maintain the serum iron content of the patient to an erythropoiesis supportable level is administered to the patient 14 days prior to EPO therapy at one or more doses per day, for example, three times a day. EPO is also administered on day 14 at one or more doses per day, preferably one dose per day. It is also possible to administer iron only several times a week, e.g. two or three doses per week. This treatment regimen is then continued each day until the hematocrit of the patient reaches a desired level. Variations of this regimen, such as alternating EPO and/or iron treatment on every second or third day, would be determined by the skilled practitioner. A preferred total treatment period is about 21 days beginning with the first day of EPO therapy. If the patient has adequate iron stores prior to the start of therapy then it is not necessary to start him on iron therapy before EPO is administered. Pre-therapy with iron will be necessary in patients having low iron stores.

The invention will be further clarified by consideration of the following examples, which are intended to be purely exemplary of the use of the invention.

EXAMPLE 1

Recombinantly produced human-EPO (Amgen Corporation, Thousand Oaks, Calif.) was used. The specific activity of the recombinant human-EPO was 129,000 units per milligram of hormone. One unit of EPO is that quantity which provides a response similar to 5 micromoles of Cobalt as is described in The Johns Hopkins Medical Journal (1980), Vol. 146 at pp. 311–320. The recombinant human-EPO was greater than 99% pure and formulated in a buffered saline solution containing 2.5 mg/ml human serum albumin. Placebo doses were formulated identically except for the lack of EPO.

Four healthy adult volunteers (age 18–45) were selected for the study. One additional patient was selected as a control and treated with placebo. The following is a partial list of the criteria used to select the patients. Each patient did not have clinically significant abnormal values for the following hematology tests: hemoglobin, hematocrit (did not exceed the upper limit of the laboratory normal range); total erythrocyte count (did not exceed the upper limit of the laboratory normal range); total leucocyte count, including differential; platelet count; and reticulocyte count. Each patient did not have clinically significant abnormal values for the standard serum chemistry tests, urinalysis, serum iron and TIBC. At baseline, ferritin levels were low. Additionally, each patient had a normal erythropoietin plasma level.

The normal human subjects were first treated with EPO alone (i.e., without iron supplementation) over a 17 day period. The dosing regimen was 200 U/kg of body weight by I.V. bolus injection on days 1 and 4–17 for three of the subjects. The fourth subject received 300 U/kg. The control subjects were treated identically to those subjects who received EPO. As can be seen from FIG. 1 and Table 1, there was no significant difference in hematocrit, hemoglobin or reticulocyte levels between Day 1 and Day 17.

In the second part of the study, each subject (including the control subject) was given ferrous sulfate tablets at approximately 300 milligrams 3 times each day (i.e., 900 mg per day) for two weeks prior to EPO administration and continued daily throughout the treatment period. After iron loading, the subjects were treated with the same EPO dose regimen described above. As can be seen from FIG. 2 and Table 2, the subjects had a brisk reticulocytosis and increase in hematocrit and hemoglobin after iron loading.

A comparison of the results listed in Tables 1–4 reveals the importance of adequate iron availability in normal human patients in order to enable a clinically meaningful erythropoietic response to EPO. The data in Tables 1 and 2 are the summaries of the data of the four subjects tested, except that the serum iron values in Table 1 for Days 1 and 10 are only for three of the patients. The Day 10 and Day 17 results are expressed as the unit change (increase or decrease) from the Baseline values. Tables 3 and 4 represent the data for placebo treated patients before and after iron loading, respectively. The Table 3 values are the mean values for three patients (except for Day 10 ferritin and serum iron, where only two patients were measured). The Table 4 values are for one patient. The Baseline values for Tables 1 and 3 are pre-study for ferritin and Day 1 (Pre-dose) for the other variables. The Baseline values for Tables 2 and 4 are Day 1 (Pre-dose) for all variables.

TABLE 1

SUMMARY OF RETICULOCYTE COUNT, HEMATOCRIT, FERRITIN AND SERUM IRON RESULTS FOR EPO SUBJECTS BEFORE IRON LOADING

|  |  | Baseline | Day 10 Change | Day 17 Change |
|---|---|---|---|---|
| Reticulocyte Count ($\times 10^3/mm^3$) | Mean | 96.70 | 23.08 | 67.45 |
|  | Std. Dev. | 50.34 | 41.02 | 70.75 |
| Hematocrit (%) | Mean | 46.62 | 1.32 | 2.08 |
|  | Std. Dev. | 4.48 | 2.69 | 3.84 |
| Ferritin (ng/ml) | Mean | 15.98 | −9.72 | −11.45 |
|  | Std. Dev. | 7.67 | 5.81 | 6.92 |
| Serum Iron (mcg/dl) | Mean | 62.67 | −37.33 | −43.50 |
|  | Std. Dev. | 25.11 | 38.79 | 22.17 |

TABLE 2

SUMMARY OF RETICULOCYTE COUNT, HEMATOCRIT, FERRITIN AND SERUM IRON RESULTS FOR EPO SUBJECTS AFTER IRON LOADING

|  |  | Baseline | Day 10 Change | Day 17 Change |
| --- | --- | --- | --- | --- |
| Reticulocyte Count ($\times 10^3/mm^3$) | Mean | 91.78 | 386.18 | 577.14 |
|  | Std. Dev. | 42.38 | 120.57 | 75.09 |
| Hematocrit (%) | Mean | 45.70 | 4.52 | 7.40 |
|  | Std. Dev. | 2.97 | 1.61 | 2.16 |
| Ferritin (ng/ml) | Mean | 47.60 | −19.50 | −30.65 |
|  | Std. Dev. | 12.03 | 4.67 | 8.64 |
| Serum Iron (mcg/dl) | Mean | 105.00 | −75.25 | −76.50 |
|  | Std. Dev. | 54.26 | 52.09 | 55.38 |

TABLE 3

PLACEBO TREATED PATIENTS BEFORE IRON LOADING

|  | Baseline | Day 10 Change | Day 17 Change |
| --- | --- | --- | --- |
| Reticulocyte Count ($\times 10^3/mm^3$) | 122.6 | −41.6 | −36.7 |
| Hematocrit (%) | 48.4 | −0.9 | −0.9 |
| Ferritin (ng/ml) | 6.1 | 2.7 | 0.2 |
| Serum Iron (mcg/dl) | 52.3 | 4.7 | −28.3 |

TABLE 4

PLACEBO TREATED PATIENT AFTER IRON LOADING

|  | Baseline | Day 10 Change | Day 17 Change |
| --- | --- | --- | --- |
| Reticulocyte Count ($\times 10^3/mm^3$) | 48.2 | 48.4 | 12.2 |
| Hematocrit (%) | 45.3 | 0.4 | 1.5 |
| Ferritin (ng/ml) | 19.8 | 3.0 | −2.3 |
| Serum Iron (mcg/dl) | 39.0 | 3.0 | 38.0 |

When considering the control data presented herein, it should be noted that it is well known that iron supplementation alone in pharmacologic doses will not increase the hematocrit of a normal patient having adequate iron stores. This phenomenon was recognized in the study of a disease called primary hemochromatosis in which patients absorb excess iron through the gastrointestinal tract. These patients may, in fact, die of the effects of excessive tissue iron stores. However, despite massive iron overload, they do not develop polycythemia (an increased number of red blood cells in the blood). This is demonstrated in the classic article by Finch et al. on ferrokinetics (Finch, C. A. et al., "Ferrokinetics in Man", in *Medicine,* Vol. 49, No. 11, pp. 17–48 (1970)). Specifically, page 43 of Finch et al. indicates that there is a normal hematocrit in 10 patients with primary hemochromatosis despite their state of iron overload. This "experiment of nature" indicates that increasing iron stores beyond physiological values does not increase erythropoiesis beyond normal levels.

Tables 1 and 2 show that in the face of depleted iron stores, EPO has no hematologic effect in normal human patients. Prior to iron loading, EPO had a minimal effect on erythropoiesis: there was no significant difference in reticulocyte count and hematocrit when compared to the control. After iron loading there were significant increases in mean reticulocyte count and mean hematocrit in the EPO subjects. The combined effect of EPO and iron was so marked that the study medication was discontinued early for all subjects.

These experiments conclusively demonstrate that in normal subjects with adequate iron stores, a combined treatment of EPO and iron is effective in stimulating erythropoiesis.

EXAMPLE 2

This example concerns a double-blind, placebo-controlled study to determine whether recombinant human EPO can facilitate presurgical autologous blood donation. The study population consisted of 54 patients between the ages of 18 to 25 years who were scheduled for orthopedic surgery, which was to occur within 25 to 35 days after receiving the first dose of study medication. The dosing regimen consisted of 6 doses of recombinant human EPO (600 U/kg) or placebo (diluent) by IV bolus, each dose administered every 3 to 4 days over a 21 day period.

At each study visit a complete blood count was obtained from each patient prior to dosing. If the patient's hematocrit level was greater than or equal to 34%, a unit of blood was collected and stored for autologous transfusion. A unit of blood is approximately equal to one pint. If the patient's hematocrit was less than 34%, no blood donation was made. The hematocrit cutoff level of 34% was chosen because it is the American Association of Blood Banks standard for autologous donation (levels below this number render a patient too anemic to donate blood). However, each patient received study medication at each of the 6 visits whether or not a unit of blood was donated. All patients received oral iron supplementation three times daily throughout the study.

Prior to the present invention, the amount of blood a patient could pre-donate before elective surgery was limited by the time frame in which his blood could be kept "fresh" and also the capacity of his body to produce new blood during this time frame. A patient could pre-donate blood any time before surgery but usually, autologous blood was not pre-donated more than about 35 days prior to elective surgery. The reason for this is that blood stored in liquid form is generally not viable after 35 days. If surgery is scheduled more than 35–42 days from donation, the blood must be frozen, but most surgeons prefer to work with fresh blood rather than frozen blood. In order to prevent the patient from becoming anemic, the typical patient was only able to donate about 3–4 units of blood (less than half a person's total blood supply) over the 35 day period that his blood was kept in liquid form.

The present invention not only provides a means for increasing the yield of blood that can be pre-donated but it also attenuates the problem of presurgical anemia that occurs with prior methods of autologous transfusion. By using the present method, about 5–6 units of blood can be obtained from a patient within a 35 day or shorter time period and that patient's hematocrit will be maintained at or above normal levels thereby preventing a state of anemia from occurring. Use of the present method will attenuate the drop in hematocrit due to phlebotomy. Such a treatment regimen will allow the patient to go to surgery with a higher hematocrit and more stored blood than is possible if the present method is not used.

A preferred regimen for autologous transfusion may begin, for example, by starting a patient on iron therapy about one week before the first blood donation. The iron may be administered from one to three times per day. It should be noted that iron supplementation, although preferred, may not be necessary in all cases, especially when the patient already has adequate iron stores or very high iron stores, such as in hemochromatosis. It is believed that EPO alone will have an adequate effect in such individuals. After iron supplementation begins, over the next 21–35 days the patient is bled two times a week with about one unit of blood being withdrawn each time. The time span over which blood is withdrawn may be greater than 35 days, but then the collected blood may have to be frozen. At each bleeding the patient is given a dose of EPO in order to maintain the patient's hematocrit at or near its starting value. The EPO is given to the patient whether or not blood is withdrawn. The EPO and iron may be administered to the patient in any manner or regimen as previously mentioned herein. For instance, if the patient is a male with a hematocrit of 45% before his first bleeding, his hematocrit will be monitored over the treatment period with the goal being to maintain the hematocrit at or near the range 34%–45% in order to prevent was collected. Recombinant human EPO (600 U/kg) or placebo was then administered by I.V. bolus. Blood pressure and pulse rate were recorded before blood was collected and prior to discharge from the clinic for that visit (i.e., after study medication was administered). This procedure was repeated every 3 or 4 days for a planned total of six units of blood to be collected over 21 days. A study termination visit (visit 7) was planned within 5 days of the last study visit (visit 6). At this time a comprehensive evaluation, including appropriate laboratory tests, was performed. A complete blood count was performed within 24 hours prior to surgery. Estimated blood loss and the number of units of autologous and homologous blood administered during and following the surgery were recorded.

The results of these studies are set forth in Tables 5–7. Table 5 shows that patients treated according to the present invention were able to pre-donate more autologous blood than placebo patients and the EPO patients required less homologous blood in their surgeries than the placebo patients (2 units vs. 5 units).

TABLE 5

| COMPARISON OF AUTOLOGOUS/DONATION AND AUTOLOGOUS/HOMOLOGOUS TRANSFUSION REQUIREMENTS | | | | | | |
|---|---|---|---|---|---|---|
| Treatment | N | No. of Units Donated | Mean No. of Units Donated | Range of No. of Units Donated | No. of Autol. Units Transfused | No. of Homol. Units Transfused |
| EPO | 23 | 125 | 5.43 | 3–6 | 89 | 2 |
| PLACEBO | 24 | 99 | 4.13 | 2–6 | 73 | 5 | the patient from becoming severely anemic. The use of EPO prevents the anemia from occurring because it induces a rapid acceleration of erythropoiesis and thereby attenuates the drop in hematocrit from phlebotomy.

The patients in the present study were divided into two treatment groups: EPO treated (23 patients) and placebo treated (24 patients). On pre-study examination (visit 0) the patients were evaluated by medical history, physical examination, electrocardiogram, and blood, urine, and stool test. These tests were repeated during the study and/or at study termination (visit 7). The patients who had medical conditions that might interfere with the evaluation of safety or efficacy of the study treatment were excluded from the study.

At the beginning of the study, the patients were placed on an oral iron preparation that was continued throughout the study. At the first visit, a blood count was obtained and if the hematocrit was equal to or greater than 34%, a unit of blood Table 6 shows that the present invention significantly ($P<0.05$) increases the probability of obtaining 4 or more units of autologous blood from a patient. The percentage of patients unable to donate 4 or more units of blood was 4.3% for EPO treated patients and 29.2% for placebo treated patients.

TABLE 6

| | NUMBER OF UNITS OF AUTOLOGOUS BLOOD DONATED | | | | | | |
|---|---|---|---|---|---|---|---|
| TREATMENT | N | 1 UNIT | 2 UNITS | 3 UNITS | 4 UNITS | 5 UNITS | 6 UNITS |
| EPO | 23 | 0 | 0 | 1 | 3 | 4 | 15 |
| PLACEBO | 24 | 0 | 1 | 6 | 9 | 5 | 3 |

Table 7 shows that the hematocrit of the EPO treated patients decreased by about 12.9% between pre-study and post-study values. The hematocrit of the placebo patients decreased by about 20.5%. Thus, use of the present invention maintained the hematocrit within the range of 10–25% of its original value and it went no lower than about 34%.

TABLE 7

| MEAN HCT, HGB AND RETICULOCYTE COUNTS (PRE-STUDY, POST-STUDY AN PRE-OPERATIVE) | | | | | | |
|---|---|---|---|---|---|---|
| PARAMETER | TREATMENT | PRE-STUDY | POST-STUDY | CHANGE PRE-POST | PRE-OP | DISCHARGE |
| HEMATOCRIT (%) | EPO | 43.5 | 37.9 | −5.5** | 38.8 | 33.8 |
| | PLACEBO | 42.3 | 33.6 | −8.7** | 34.7 | 30.9 |
| HEMOGLOBIN (GM/DL) | EPO | 14.4 | 12.1 | −2.3** | — | — |

TABLE 7-continued

MEAN HCT, HGB AND RETICULOCYTE COUNTS
(PRE-STUDY, POST-STUDY AN PRE-OPERATIVE)

| PARAMETER | TREATMENT | PRE-STUDY | POST-STUDY | CHANGE PRE-POST | PRE-OP | DISCHARGE |
|---|---|---|---|---|---|---|
| | PLACEBO | 14.2 | 11.1 | −3.1** | — | — |
| RETICULOCYTE | EPO | 1.55 | 6.71 | +5.16* | — | — |
| COUNT (%) | PLACEBO | 1.91 | 5.20 | +3.39* | — | — |

*P < 0.05
**P < 0.01

The result of these studies can be summarized as follows. Patients treated according to the present invention donated significantly more units of blood (5.4 vs. 4.1 units) than patients receiving placebo. Patients receiving EPO and iron had a significantly reduced decline in hematocrit (−5.5% vs. −8.7%) than patients receiving placebo. There was a significantly increased proportion of patients donating 4 or more units of blood in the EPO/iron treated patients compared to the placebo patients (95.7% vs. 70.8%). Finally, EPO was well tolerated at a dose of 600 U/kg, I.V., twice weekly for three weeks.

This study shows that the benefits of autologous blood over homologous blood for transfusion are clear in light of the risks of blood-transmitted diseases. The present methods will be useful for any patient who anticipates requiring three or more units of blood for transfusion purposes during surgery.

Other embodiments of the invention will be apparent to one skilled in the art from a consideration of this specification or practice of the invention disclosed herein. It is intended that the specification and examples be considered as exemplary only, with the true scope and spirit of the invention being indicated by the following claims.

What is claimed is:

1. A method for increasing the amount of blood that can be withdrawn from a human patient for blood transfusion purposes comprising administering to said patient a hematocrit increasing effective amount of erythropoietin in a pharmaceutically acceptable form, and administering to said patient an effective amount of iron, in a pharmaceutically acceptable form, sufficient to increase the serum iron content of the patient to an erythropoiesis supportable level.

2. A method for increasing the amount of blood that can be withdrawn from an iron enriched human patient previously given iron supplementation, said method comprising administering to said patient a hematocrit increasing effective amount of erythropoietin in a pharmaceutically acceptable form.

3. A method for maintaining the hematocrit in a human patient undergoing phlebotomy for transfusion purposes, comprising:

administering to said patient erythropoietin, in a pharmaceutically acceptable form, and in conjunction with the step of administering to said patient an effective amount of iron, in a pharmaceutically acceptable form, sufficient to increase the serum iron content of the patient to an erythropoiesis supportable level.

4. A method for increasing the amount of blood a human patient can donate for transfusion purposes, comprising:

(a) administering to said patient an effective amount of iron, in a pharmaceutically acceptable form, sufficient to increase the serum iron content of the patient to an erythropoiesis supportable level;

(b) withdrawing blood from said patient; and (c) administering to said patient a hematocrit increasing effective amount of erythropoietin, in a pharmaceutically acceptable form.

5. The method of claim 4, which is carried out once every three or four days over a period of about 21–35 days.

6. The method of claim 4, wherein the iron is administered from one to three times per day.

7. The method of claim 4, wherein about one unit of blood is withdrawn.

8. The method of claim 4, wherein 4 to 6 units of blood are collected over a period of 21–35 days.

9. The method of claim 8, wherein about one unit of blood is collected every 3 or 4 days.

10. The method of claim 4, wherein the blood is withdrawn for autologous transfusion purposes.

11. A method for increasing the hematocrit of a non-anemic human patient, comprising the steps of:

(a) administering to said patient a hematocrit increasing effective amount of erythropoietin, in a pharmaceutically acceptable form, and in conjunction with the step of (b) administering to said patient an effective amount of iron, in a pharmaceutically acceptable form, sufficient to increase the serum iron content of the patient to an erythropoiesis supportable level.

12. The method of claim 11, wherein the erythropoietin is administered parenterally.

13. The method of claim 12, wherein the parenteral administration is intravenous, intramuscular or subcutaneous injection.

14. The method of claim 11, wherein the hematocrit increasing effective amount of erythropoietin is in the range of about 15 to about 1500 units per kilogram of body weight per day.

15. The method of claim 11, wherein the amount of erythropoietin is administered from one time per day to about 3 times per week.

16. The method of claim 11, wherein the erythropoietin is administered over a period of from about 4 to about 35 days.

17. The method of claim 11, wherein the iron is administered as an oral preparation.

18. The method of claim 11, wherein the effective amount of iron is in the range of about 100 to about 1500 milligrams of iron per day.

19. The method of claim 11, wherein the amount of iron is administered from one to three times per day.

20. The method of claim 11, wherein the iron is administered over a period of from about 1 to about 21 days prior to initiation of erythropoietin therapy.

21. The method of claim 20, wherein the iron is administered daily over the treatment period.

22. A method for increasing the amount of blood that can be withdrawn from a human patient for blood transfusion purposes, comprising:

(a) administering to the patient a hematocrit increasing effective amount of erythropoietin, in a pharmaceutically acceptable form, and in conjunction with the step of (b) administering to the patient an effective amount of iron, in a pharmaceutically acceptable form, sufficient to increase the serum iron content of the patient to an erythropoiesis supportable level.

\* \* \* \* \*